United States Patent [19]

Johnson et al.

[11] Patent Number: 6,040,476
[45] Date of Patent: Mar. 21, 2000

[54] CARBON DIOXIDE ASSISTED HYDROLYSIS OF AMINOPHOSPHONATES

[75] Inventors: Todd J. Johnson, O'Fallon; William H. Miller, Glendale, both of Mo.

[73] Assignee: Monsanto Company, St. Louis, Mo.

[21] Appl. No.: 09/173,103

[22] Filed: Oct. 15, 1998

Related U.S. Application Data

[60] Provisional application No. 60/062,351, Oct. 15, 1997.

[51] Int. Cl.⁷ .................................................... C07F 9/38
[52] U.S. Cl. ................................................. 562/1; 562/11
[58] Field of Search ........................... 562/23, 16, 17, 562/11

[56] References Cited

U.S. PATENT DOCUMENTS 4,439,373   3/1984   Nagubandi ............................. 562/17
4,548,760   10/1985  Nagubandi ............................. 562/17

OTHER PUBLICATIONS

Advanced Inorganic Chemistry by Cotton and Wilkinson, pp. 296–297, 1972.
Advanced Organic Chemistry by March, 1986.

*Primary Examiner*—Gary Geist
*Assistant Examiner*—Jean F Vollano
*Attorney, Agent, or Firm*—James M. Warner; Arnold White & Durkee

[57] ABSTRACT

The invention provides a process for preparing aminophosphonic acids comprising contacting an aminophosphonate ester with a base in the presence of a hydrolysis facilitator selected from the group consisting of $CO_2$, $CS_2$ and COS. In one embodiment, the aminophosphonate ester is first prepared by contacting an amine, trialkylphosphite, base and formaldehyde.

48 Claims, No Drawings

CARBON DIOXIDE ASSISTED HYDROLYSIS OF AMINOPHOSPHONATES

This application claims the benefit of U.S. provisional application Ser. No. 60/062,351 filed Oct. 15, 1997.

BACKGROUND OF THE INVENTION

This invention relates to processes for preparing aminophosphonic acids.

This invention relates to a process for preparing aminophosphonic acids, such as N- phosphonomethylglycine, known also by its common name glyphosate. Glyphosate is a highly effective and commercially important phytotoxicant useful in controlling a large variety of weeds and crops. It is applied to the foliage of a very broad spectrum of perennial and annual grasses and broad-leafed plants to achieve the desired control. Industrial uses include control of weeds along roadsides, waterways, transmission lines, in storage areas, and in other nonagricultural areas. Usually glyphosate is formulated into herbicidal compositions in the form of its various salts which retain the anionic form of glyphosate in solution, preferably in water.

Amine phosphonomethylation to produce an aminophosphonic acid using formaldehyde and di- or trialkylphosphites has been shown in the literature, e.g., U.S. Pat. No. 5,041,628; Polish Patent Nos. 136,276 and 159,424. Such phosphonomethylation produces aminophosphonate esters that must be hydrolyzed to obtain the desired aminophosphonic acid. Prior approaches to hydrolyzing the esters have used an acid such as hydrochloric acid, or a base such as sodium hydroxide. A common problem with these types of hydrolysis is that under basic conditions N- alkylation of aminophosphonate often occurs. When hydrochloric acid is used for hydrolysis, alkyl chloride formation also occurs. The formation of such by-products decreases the yield of the desired aminophosphonic acid and requires more extensive separation of the aminophosphonic acid from the resulting reaction mixture.

An economically and technically better method for hydrolyzing aminophosphonate esters that proceeds with high conversion and selectivity to aminophosphonic acid and avoids by-product formation is therefore desirable.

SUMMARY OF THE INVENTION

This invention relates to a process for preparing aminophosphonic acids which comprises contacting in an aqueous medium an aminophosphonate ester with a base in the presence of a hydrolysis facilitator selected from the group consisting of $CO_2$, $CS_2$ and COS. This invention also relates to a process for preparing aminophosphonic acids which comprises contacting an amine, trialkylphosphite, alkali metal hydroxide and formaldehyde to produce a reaction mixture, and hydrolyzing the reaction mixture in the presence of a hydrolysis facilitator and base. In one embodiment, alcohol that is produced during hydrolysis is removed using pressurized carbon dioxide at a suitable flow rate.

DESCRIPTION OF ILLUSTRATIVE EMBODIMENTS

The invention relates to a process for preparing aminophosphonic acids represented by the formula

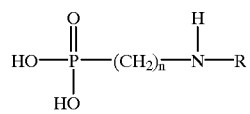

wherein n is 1 to about 3 and R is hydrogen, an alkyl group containing 1 to about 6 carbon atoms, an aryl group containing 6 to about 12 carbon atoms, carboxylate salt or ester, or hydroxyethyl, comprising contacting in an aqueous medium an aminophosphonate ester with a base in the presence of a hydrolysis facilitator selected from the group consisting of $CO_2$, $CS_2$ and COS. Typically, at least 0.5 equivalents of base is added. Alternatively, the aminophosphonate ester can first be made by contacting an amine represented by the formula $RNH_2$ wherein R is as described in the formula above, trialkylphosphite wherein the alkyl group contains 1 to about 6 carbon atoms, alkali metal hydroxide and formaldehyde.

Aminophosphonate esters suitable in the processes of the present invention have the general formula:

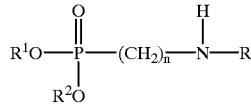

wherein R is hydrogen, $C_{1-6}$ alkyl, $C_{6-12}$ aryl, a substituted aryl, $(C_{6-12})aryl(C_{1-6})alkyl$, $—(CH_2)_n—CO_2R^3$ or $—(CH_2)_m—OR^3$; $R^1$ and $R^2$ are independently hydrogen, $C_{1-6}$ alkyl, $C_{6-12}$ aryl, $(C_{6-12})aryl(C_{1-6})alkyl$, or a salt forming cation such as $Na^+$, $K^+$, $[(C_{1-6})alkyl]NH_3^+$, $[(C_{1-6})alkyl]_2NH_2^+$ or $[(C_{1-6})alkyl]_3NH^+$; $R^3$ is hydrogen, $C_{1-6}$ alkyl, $C_{6-12}$ aryl, $(C_{6-12})aryl(C_{1-6})alkyl$, a substituted aryl, or a salt forming cation such as $Na^+$, $K^+$, $[(C_{1-6})alkyl]NH_3^+$, $[(C_{1-6})alkyl]_2NH_2^+$ or $[(C_{1-6})alkyl]_3NH^+$; n is between 1 and about 6; and m is between 2 and about 6. Preferably, the aminophosphonate ester is the mono- or diethylester of glyphosate, or the mono- or dimethylester of glyphosate.

Bases useful in the processes of the present invention are suitably alkali metal hydroxides, such as sodium hydroxide, potassium hydroxide, lithium hydroxide and cesium hydroxide; alkaline earth metal hydroxides, such as calcium hydroxide; and tertiary amines, such as triethylarmine. Preferably the base is sodium hydroxide. Generally, the number of equivalents of base added will be in the range of 0.5 to about 3.0 equivalents, preferably 1.5 to about 2.0 equivalents.

The production of aminophosphonic acids from aminophosphonate esters is conducted in the presence of a hydrolysis facilitator selected from the group consisting of $CO_2$, $CS_2$ and COS. Preferably, $CO_2$ is used as the hydrolysis facilitator. When $CO_2$ is the hydrolysis facilitator, the $CO_2$ is desirably pressurized to between about 10 and about 500 psi, and more preferably pressurized to between 150 and about 400 psi.

The production of aminophosphonic acids from aminophosphonate esters is conducted at a suitable temperature which can vary over a wide range. The reaction temperature will generally be within the range of about 75° C. to about 120° C., preferably about 100° C. The hydrolysis reaction is conducted for a suitable time which can vary over a wide range depending on various parameters, e.g. the reaction temperature. Generally, the reaction time will be within the range of the time necessary for the phosphonate esters to be hydrolyzed to about 6 hours, preferably about 1 hour to about 4 hours. The production of aminophosphonic acids is also conducted at a suitable pH, which is generally in the range of about 5 to about 14, preferably at a pH of about 7 to about 10.

The production of aminophosphonic acids from aminophosphonate esters may be conducted while removing alcohol that is produced in the reaction. Preferably, the alcohol removal is conducted by introducing pressurized $CO_2$ at a suitable flow rate. The flow rate is generally between about 0.1 and about 1000 mL/min, preferably between about 100 and about 200 mL/min per mole of aminophosphonate ester. The pressure of the $CO_2$ is preferably about 400 psi.

As previously mentioned, the aminophosphonate ester can first be made by contacting an amine, trialkylphosphite, base and formaldehyde. The formaldehyde can be employed according to the invention as paraformaldehyde or as an aqueous solution of formaldehyde. Aqueous formaldehyde is commercially available as 37–50% by weight aqueous solutions which may contain methanol, ethanol, or n-butanol. The amount of formaldehyde utilized in the processes of the invention can be expressed as a molar ratio of formaldehyde starting material to phosphite starting material. Broadly, the molar ratio of formaldehyde to phosphite is about 1:1 to about 5:1, preferably about 1:1 to about 2:1, and most preferably about 1:1 to 1.5:1.

Trialkylphosphites, useful in the processes of the invention, are commercially available. Trialkylphosphites can be represented by the formula $P(OR)_3$ wherein R is an alkyl group. The alkyl groups of the trialkylphosphites are linear or branched alkyl groups having 1 to about 6 carbon atoms and are optionally substituted with —OH groups. Trialkylphosphites are preferred over dialkylphosphites because of unexpectedly improved yields achievable with the trialkylphosphites.

Amines useful in the processes of the present invention can be represented by the formula $RNH_2$, wherein R is hydrogen, alkyl, aryl, carboxylate salt or ester, or hydroxyethyl. The preferred amine is glycine. Many amines useful in the processes of the present invention are commercially available. The amount of amine utilized in the processes of the invention can be expressed as a molar ratio of amine starting material to phosphite starting material. Broadly, the molar ratio of amine to phosphite is about 1:1 to about 5:1, and preferably about 1:1 to about 2.5:1.

The reaction of amine, phosphite and formaldehyde is conducted at a suitable temperature which can vary over a wide range. The reaction temperature will generally be within the range of about 20° C. to about 110° C., preferably about 40° C. to about 75° C. The reaction of amine, phosphite and formaldehyde is conducted for a suitable time which can vary over a wide range depending on various parameters, e.g. the reaction temperature.

The reaction of amine, phosphite and formaldehyde can optionally be conducted in the presence of an alcohol solvent wherein the alcohol is represented by the formula $R'(OH)_m$ wherein R' is an alkyl group having 1 to about 6 carbon atoms and m is 1 to about 3. The alkyl group, R', can be linear or branched and preferably is the same alkyl group as that utilized in the trialkylphosphite starting material. Examples of suitable alcohols include, but are not limited to, methanol, ethanol, isopropanol, n-butanol and mixtures thereof.

The reactions of the present invention can optionally be carried out in an aqueous or aqueous-alcoholic medium. Preferably, the alcohol used is ethanol or methanol. The reaction mixture produced by contacting formaldehyde, amine and phosphite can optionally be diluted with water prior to hydrolysis. After the hydrolysis reaction is completed, the aminophosphonic acid can be recovered by any conventional method known to those skilled in the art.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

This example illustrates the production of glyphosate from glycine and triethylphosphite following carbon dioxide assisted hydrolysis of the resulting reaction mixture.

Glycine (15.5 g, 200 mmol), 50% sodium hydroxide (12.0 g, 150 mmol) and 6.0 g of water were mixed to form a solution. 37% Formaldehyde (8.52 g, 105 mmol) and 10 mL of ethanol were added. The temperature was adjusted to 50° C. Triethylphosphite (16.62 g, 50 mmol) was added over 30–45 minutes with the temperature being maintained at 50° C. After the addition, the reaction was maintained at 50° C. for an additional 45 minutes to complete the phosphonomethylation reaction.

The reaction mixture was next saturated with gaseous carbon dioxide which modified the pH of the solution to between 7 and 8, caused excess glycine to precipitate, and initiated a substantial amount of hydrolysis. The glycine can optionally be removed. The reaction mixture was then placed under carbon dioxide pressure at 200 psi and heated to 100–120° C. to complete the hydrolysis, which took about 2–4 hours.

Isolation of glyphosate occurs as normal following appropriate adjustment of the reaction mixture pH. Yields of glyphosate up to 92% based on the phosphite used have been obtained.

Examples 2 and 3 exemplify the effect of removing alcohol on the selectivity and yield of the $CO_2$ assisted hydrolysis of glyphosate esters.

EXAMPLE 2

An autoclave was charged with a solution containing the di- and monoethylester of glyphosate (0.45 mol), NaOH (0.250 mol), water and ethanol. The pH of this solution was 7.6. Then 400 psi $CO_2$ (static) was established and the solution was heated to 100° C. After 18 h, the conversion of the aminophosphonate esters to aminophosphonic acids was 100%. The chemical yield of glyphosate was 74% (0.370 mol). The selectivity for the conversion of the aminophosphonate esters to glyphosate and N-ethylglyphosate was 92% and 8%, respectively.

EXAMPLE 3

An autoclave was charged with the same solution as described in Example 2. To remove ethanol from the reactor during hydrolysis, 400 psi $CO_2$ was established with a flow rate of 100 mL/min. The solution was heated to 100° C. After 5.5 h, the conversion of the aminophosphonate esters to aminophosphonic acids was 100%. The chemical yield of glyphosate was 81% (0.405 mol). The selectivity for the conversion of the aminophosphonate esters to glyphosate was 100%, while no N-ethylglyphosate was detected.

EXAMPLE 4

This example exemplifies the effect of pH on the selectivity and yield of the $CO_2$ assisted hydrolysis of glyphosate esters.

An autoclave was charged with a solution containing the di- and monoethylester of glyphosate (0.34 mol), NaOH (0.250 mol), water and ethanol. The pH of this solution was then adjusted to 5.6 with trifluoroacetic acid. Then 400 psi $CO_2$ (static) was established and the solution was heated to 100° C. After 7.5 h, the conversion of the aminophosphonate esters to aminophosphonic acids was 41%. The chemical yield of glyphosate was 29% (0.081 mol). The selectivity for the conversion of the aminophosphonate esters to glyphosate and N-ethylglyphosate was 70% and 30%, respectively.

The pH of this sample was then adjusted from 4.4 to 8.4 with NaOH. Then 400 psi $CO_2$ (static) was established and the solution was heated to 100° C. After 5 h, the conversion of the remaining aminophosphonate esters to aminophosphonic acids was complete. The final chemical yield of glyphosate was 56% (0.28 mol). No further production of N-ethylglyphosate was observed.

EXAMPLE 5

This example illustrates the removal of excess glycine prior to complete $CO_2$ assisted hydrolysis of glyphosate esters. This example also illustrates the dilution of the reaction mixture with water to avoid precipitation with no apparent effect on the rate or selectivity of the hydrolysis.

A mixture containing the di- and monoethylester of glyphosate (0.45 mol), glycine (0.50 mol), NaOH (0.50 mol), water (60 g) and ethanol (50 mL) was heated to 50° C. Then $CO_2$ was bubbled through the mixture for 3 h. During the addition of $CO_2$ a white precipitate formed, which was collected by filtration after the reaction mixture had cooled to room temperature. This solid was assayed to be 74.4% glycine and 1.3% glyphosate. The mole percent of phosphorous species in the filtrate was assayed to be 17.1% glyphosate, 69.7% monoethylester of glyphosate and 13.4% other.

A 50 mL microclave was charged with a 20 g portion of the filtrate and 20 g of water, and was heated to 110° C. Assay of an aliquot removed at this time revealed that the solution contained 43.2% glyphosate, 46.3% monoethylester of glyphosate and 10.4% other. Then 400 psi $CO_2$ was established over the solution. After 5 h, the solution contained 91.7% glyphosate, 1.4% monoethylester of glyphosate and 6.9% other for a 102% conversion to glyphosate based on the di- and monoethylester of glyphosate. Based on the original charge of $P(OEt)_3$, a 93% chemical yield of glyphosate was realized after $CO_2$ hydrolysis.

EXAMPLE 6

This example illustrates a process where base (NaOH) was added prior to the introduction of $CO_2$.

A 50 mL autoclave was charged with a 20 g portion of an alkaloida stream, as defined in U.S. Pat. No. 4,486,359 incorporated herein by reference, which had 66% of the phosphorous as dimethylester of glyphosate. An additional 20 g of water was added to this stream and its pH was adjusted to 10 with NaOH. Then 400 psi $CO_2$ was established and the solution was heated to 100° C. After 5 hours at 100° C., an aliquot was removed for analysis. Based on the original amount of dimethylester of glyphosate, the sample contained 80% glyphosate, and 20% N-methylglyphosate. There was no mono- or dimethylester of glyphosate present in the final stream.

EXAMPLE 7

This example illustrates a process where additional base was not added prior to the introduction of $CO_2$.

A 50 mL autoclave was charged with a 20 g portion of an alkaloida stream which had 66% of the phosphorous as dimethylester of glyphosate. An additional 20 g of water was added to this solution. Then 400 psi $CO_2$ was established and the solution was heated to 100° C. After 5 hours at 100° C., an aliquot was removed for analysis. Based on the original amount of dimethylester of glyphosate, the sample contained 90% monomethylester of glyphosate, 8% glyphosate, and 2% N- methylglyphosate. There was no dimethylester of glyphosate present in the final stream.

COMPARATIVE EXAMPLE 1

This example illustrates a process where additional NaOH was added, but $CO_2$ was not introduced to the system.

A 50 mL autoclave was charged with a 20 g portion of an alkaloida stream which had 66% of the phosphorous as dimethylester of glyphosate. An additional 20 g of water was added to this stream and its pH was adjusted to 10 with NaOH. Then the solution was heated to 100° C. After 5 hours at 100° C., and aliquot was removed for analysis. Based on the original amount of dimethylester of glyphosate, the sample contained 100% monomethylester of glyphosate.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A process for producing an aminophosphonic acid comprising:

contacting an aqueous medium an aminophosphonate ester with base;

adding a hydrolysis facilitator selected from the group consisting of $CO_2$, $CS_2$ and COS; and hydrolyzing the aqueous medium comprising the aminophosphonate ester, base, and hydrolysis facilitator at a temperature above about 50° C.

2. The process of claim 1 wherein the aminophosphonic acid has the formula $$HO-\underset{\underset{HO}{|}}{\overset{\overset{O}{\|}}{P}}-(CH_2)_n-\underset{}{\overset{H}{\underset{|}{N}}}-R$$

wherein n is 1 to about 3 and R is hydrogen, an alkyl group containing 1 to about 6 carbon atoms, an aryl group containing 6 to about 12 carbon atoms, carboxylate salt or ester, or hydroxyethyl.

3. The process of claim 1 wherein the molar ratio of base to aminophosphonate ester is at least about 1:2.

4. The process of claim 1 wherein the base is an alkali metal hydroxide.

5. The process of claim 4 wherein the alkali metal hydroxide is sodium hydroxide.

6. The process of claim 1 wherein the base is an alkaline earth metal hydroxide.

7. The process of claim 1 wherein the base is a tertiary amine.

8. The process of claim 1 wherein the hydrolysis facilitator is $CO_2$.

9. A process for producing an aminophosphonic acid comprising contacting in an aqueous medium an aminophosphonate ester with base in the presence of $CO_2$, wherein the pressure of the $CO_2$ is between 10 and about 500 psi.

10. The process of claim 9 wherein the pressure of the $CO_2$ is between abut 150 and about 400 psi.

11. The process of claim 1 further comprising introducing a flow of pressurized $CO_2$.

12. The process of claim 11 wherein the flow rate of $CO_2$ is between about 100 and about 200 mL/min per mole of aminophosphonate ester.

13. The process of claim 1 wherein the contacting is carried out at a pH between about 7 and about 10.

14. The process of claim 1 wherein the contacting is carried out at a temperature between about 75° C. and about 120° C.

15. The process of claim 1 wherein the aminophosphonate ester is glyphosate monoethylester, glyphosate diethylester, or a combination thereof.

16. The process of claim 1 wherein the contacting is conducted in an aqueous-alcoholic medium.

17. A process for producing an aminophosphonic acid comprising the steps of:
    contacting an amine, trialkylphosphite, base and formaldehyde to produce a first reaction mixture, and
    hydrolyzing said first reaction mixture in the presence of a separate phase comprising a
        hydrolysis facilitator selected from the group consisting of $CO_2$, $CS_2$ and COS to produce a second reaction mixture comprising aminophosphonic acid and alcohol.

18. The process of claim 17 wherein the aminophosphonic acid has the formula

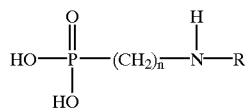

wherein n is 1 to about 3 and R is hydrogen, an alkyl group containing 1 to about 6 carbon atoms, an aryl group containing 6 to about 12 carbon atoms, carboxylate salt or ester, or hydroxyethyl.

19. The process of claim 17 wherein the amine has the formula $RNH_2$ wherein R is hydrogen, an alkyl group containing 1 to about 6 carbon atoms, an aryl group containing 6 to about 12 carbon atoms, carboxylate salt or ester, or hydroxyethyl.

20. The process of claim 17 wherein the molar ratio of base to aminophosphonate ester is at least about 1:2.

21. The process of claim 17 wherein the base is an alkali metal hydroxide.

22. The process of claim 21 wherein the alkali metal hydroxide is sodium hydroxide.

23. The process of claim 17 wherein the base is an alkaline earth metal hydroxide.

24. The process of claim 17 wherein the base is a tertiary amine.

25. The process of claim 17 wherein the hydrolysis facilitator is $CO_2$.

26. A process for producing an aminophosphonic acid comprising the steps of:
    contacting an amine, trialkylphosphite, base and formaldehyde to produce a first reaction mixture, and hydrolyzing said first reaction mixture in the presence of $CO_2$, to produce a second reaction
    mixture comprising aminophosphonic acid and alcohol,
    wherein the pressure of the $CO_2$ is between about 10 and about 500 psi.

27. The process of claim 26 wherein the pressure of the $CO_2$ is between about 150 and about 400 psi.

28. The process of claim 17 further comprising removing the alcohol during the hydrolysis.

29. The process of claim 28 wherein the removing comprises introducing a flow of pressurized $CO_2$.

30. The process of claim 29 wherein the flow rate of $CO_2$ between about 100 and 200 mL/min per mole of aminophosphonate ester.

31. The process of claim 17 wherein the hydrolysis is carried out at a pH between about 7 and about 10.

32. The process of claim 17 wherein the hydrolysis is carried out at a temperature between about 75° C. and about 120° C.

33. The process of claim 17 further comprising diluting the first reaction mixture with water prior to the hydrolysis.

34. The process of claim 17 wherein the amine is glycine.

35. The process of claim 17 wherein the trialkylphosphite is triethylphosphite.

36. The process of claim 9 wherein the aqueous medium is saturated with carbon dioxide.

37. The process of claim 9 wherein a gas comprising carbon dioxide is bubbled through the heated aqueous mixture.

38. The process of claim 1 further comprising contacting the heated aqueous medium with a gaseous phase comprising said hydrolysis facilitator.

39. The process of claim 11 wherein the flow rate of $CO_2$ is between about 0.1 and about 1000 mL/min per mole of aminophosphonate ester.

40. The process of claim 29 wherein the flow rate of $CO_2$ is between about 0.1 and about 1000 mL/min per mole of aminophosphonate ester.

41. The process of claim 17 further comprising bubbling a gas comprising the hydrolysis facilitator through the aqueous mixture before hydrolyzing the mixture.

42. The process of claim 41 further comprising separating out precipitated amine.

43. The process of claim 41 wherein the flow rate of $CO_2$ is between about 0.1 and about 1000 mL/min per mole of aminophosphonate ester.

44. The process of claim 26 wherein the hydrolysis is carried out at a pH between about 7 and about 10.

45. The process of claim 26 wherein the hydrolysis is carried out at a temperature between about 75° C. and about 120° C.

46. The process of claim 26 further comprising diluting the first reaction mixture with water prior to the hydrolysis.

47. The process of claim 26 wherein the amine is glycine.

48. The process of claim 26 wherein the trialkylphosphite is triethylphosphite.

* * * * *